(12) United States Patent
Jones et al.

(10) Patent No.: US 6,913,695 B2
(45) Date of Patent: Jul. 5, 2005

(54) SANITIZATION OF CHROMATOGRAPHIC MEDIA

(75) Inventors: Nathan C. Jones, Apex, NC (US); Marina N. Korneyeva, Raleigh, NC (US); James F. Rebbeor, Garner, NC (US); Richard Scott Rosenthal, Raleigh, NC (US); Christopher J. Stenland, Cary, NC (US)

(73) Assignee: Bayer HealthCare LLC, Tarrytown, NY (US)

( * ) Notice: Subject to any disclaimer, the term of this patent is extended or adjusted under 35 U.S.C. 154(b) by 170 days.

(21) Appl. No.: 10/614,904

(22) Filed: Jul. 8, 2003

(65) Prior Publication Data

US 2005/0006307 A1 Jan. 13, 2005

(51) Int. Cl.⁷ ............................................... B01D 15/08
(52) U.S. Cl. ....................... 210/635; 210/656; 210/764; 210/198.2; 210/636; 422/28; 422/37
(58) Field of Search ................................. 210/635, 656, 210/659, 764, 198.2, 501, 502.1, 636; 422/28, 37

(56) References Cited

U.S. PATENT DOCUMENTS

| | | | |
|---|---|---|---|
| 5,252,216 A | | 10/1993 | Folena-Wasserman et al. .. 210/635 |
| 5,429,746 A | | 7/1995 | Shadle et al. ................ 210/635 |
| 5,571,720 A | * | 11/1996 | Grandics et al. .......... 435/286.1 |
| 5,676,837 A | * | 10/1997 | Jungbauer et al. ........... 210/635 |
| 5,840,858 A | | 11/1998 | Smith et al. ................. 530/413 |
| 6,096,216 A | * | 8/2000 | Shanbrom et al. .......... 210/638 |
| 6,106,773 A | * | 8/2000 | Miekka et al. ................. 422/28 |
| 6,136,197 A | * | 10/2000 | Egorov et al. ............... 210/656 |
| 6,310,186 B1 | * | 10/2001 | Wilson et al. ............... 530/412 |
| 6,372,793 B1 | * | 4/2002 | Lamango et al. ........... 514/562 |
| 2003/0027125 A1 | | 2/2003 | Mills et al. .................. 435/1.1 |

FOREIGN PATENT DOCUMENTS

| | | |
|---|---|---|
| DE | 100 63 427 | 7/2002 |
| EP | 1 394 120 | 3/2004 |

OTHER PUBLICATIONS

International Search Report (PCT/US2004/020891, dated Sep. 22, 2004).
Print-out of Delphion® Search Record for DE 100 63 427.
Caughey, B., et al., "Scrapie Infectivity Correlates with Converting Activity, Protease Resistance, and Aggregation of Scrapie-Associated Prion Protein in Guanidine Denaturation Studies," *Journal of Virology*, 71(5): 4107–4110 (1997).
Lee, D.C., et al., "Monitoring plasma processing steps with a sensitive Western blot assay for the detection of the prion protein," *Journal of Virological Methods*, 84:77–89 (2000).
Manuelidis, L., "Decontamination of Creutzfeldt-Jakob Disease and other transmissible agents," *Journal of Neuro-Virology*, 3(1): 62–65 (1997).

* cited by examiner

*Primary Examiner*—Ernest G. Therkorn
(74) *Attorney, Agent, or Firm*—Womble Carlyle Sandridge & Rice, PLLC

(57) ABSTRACT

A method of sanitizing chromatographic media is provided. The method includes contacting the media with an acidic chaotropic agent, at low temperature and low pH. The method provides pathogen removal and/or inactivation, including viral inactivation in particular embodiments.

28 Claims, No Drawings

SANITIZATION OF CHROMATOGRAPHIC MEDIA

BACKGROUND

The potential for pathogen contamination of blood products remains an important medical issue throughout the world. Although improved testing methods for the presence of certain key pathogenic viruses have markedly reduced the incidence of diseases associated with administration of blood products, concerns regarding the safety of the blood supply continue. Furthermore, other viral, bacterial, and unknown agents that are not routinely tested for, remain a potential threat to administration of blood products. In addition, testing of the blood supply cannot insure the safety of blood and blood products against future unknown pathogens that may enter the donor population and potentially result in disease transmission before sensitive tests can be implemented. Although less affected by such concerns, protein therapeutics produced by recombinant or transgenic means are also subject to contamination by pathogenic agents.

An alternative approach to eliminate transmission of viral or other potential diseases through blood products is to develop a means to reduce active pathogens in blood products. Methodologies currently employed to reduce the risk of pathogen contamination of blood products include various filtration and chromatographic techniques. These process steps may be specifically dedicated to pathogen clearance or part of an overall blood product fractionation scheme. However, the preparation and maintenance of equipment used in the fractionation of blood products necessitates sanitization or decontamination, which can be difficult. For example, chromatographic fractionation of pathogen-tainted plasma intermediates may result in residual contamination of chromatographic media itself. This presents a source of potential pathogen transmission to the product stream if the media is regenerated for further use. Accordingly, a need exists for reliable sanitization of reusable chromatographic media used in the preparation of blood products.

SUMMARY OF THE INVENTION

The sanitization methods of the present invention provide methods of inactivating or removing pathogens, including viruses, that are associated with chromatographic media (which includes, but is not limited to chromatographic media, separation media, and equipment) used in the preparation of protein therapeutics, including those produced by recombinant and transgenic means. The methods are effective against a variety of pathogens. As the number of protein therapeutics increases, the usage of various chromatographic media, including specialty affinity resins, to purify these products will likely increase as well.

Accordingly, one aspect of the invention relates to a method of sanitizing hromatographic media by contacting the media with a solution of acidic chaotropic agents such as guanidine hydrochloride. In particular embodiments, acidic urea or other salts of guanidine can be used.

In another embodiment, the invention relates to a method of sanitizing chromatographic media by contacting the media with a solution of guanidine hydrochloride at a concentration of guanidine hydrochloride from about 3 molar to about 8 molar, and at a temperature from about 0° C. to about 10° C. under acidic conditions. The guanidine solution can be buffered, e.g., with 0.1 M acetic acid. In yet another embodiment, the invention relates to a method for inactivating viral contaminants associated with or adhering to chromatographic media, sufficient to allow the media to be subsequently utilized in the purification or preparation of materials for therapeutic administration, by contacting the media with a solution of guanidine hydrochloride at a concentration of guanidine hydrochloride from about 3 molar to about 8 molar, at a temperature from about 0° C. to about 10° C. under acidic conditions.

In yet another embodiment, the invention relates to a method for accomplishing viral inactivation of chromatographic resins having alkaline-labile matrices, resins having alkaline-labile ligands, and/or resins having alkaline-labile ligand linkages by contacting the resins with a solution of guanidine hydrochloride at a concentration of guanidine hydrochloride from about 3 molar to about 8 molar, and at a temperature from about 0° C. to about 10° C. at a pH from about 1 to about 5. In particular embodiments, the pH can be from about 2.5 to about 4.5. The pH, concentration of chaotropic agent, and temperature are selected such that a desired level of sanitization is achieved without significantly impairing useful characteristics of the chromatographic media. In one embodiment, the desired level of sanitization is a level that is sufficient to allow subsequent use of the media in preparation of products for therapeutic use in animals or humans. The methods of the invention can include recovery and testing of media to verify particular levels of sanitization and/or retention of desirable or required characteristics.

DESCRIPTION OF THE INVENTION

In one aspect, the invention relates to a method of sanitizing chromatographic media by contacting the media with a solution of acidic guanidine hydrochloride. Sanitization according to the invention can include viral inactivation. In particular embodiments, the viral inactivation is sufficient to allow the sanitized media to be subsequently utilized in the purification or preparation of materials for therapeutic administration.

In one embodiment, the chromatographic media can be exposed to the solution of guanidine hydrochloride at a temperature from about 0° C. to about 10° C. under acidic conditions. The temperature can be about 4° C. The solution of guanidine hydrochloride can be at a concentration of guanidine hydrochloride from about 3 molar to about 8 molar. The concentration of guanidine hydrochloride can also be about 7 molar. The solution of guanidine hydrochloride can be at a pH from about 2.5 to about 4.5.

In another embodiment, the chromatographic media can be a resin having an alkaline-labile matrix and/or a resin having an alkaline-labile ligand or ligands.

In another aspect, the invention relates to a method of sanitizing chromatographic media by contacting the media with a solution of guanidine hydrochloride at a concentration of guanidine hydrochloride from about 3 molar to about 8 molar, and at a temperature from about 0° C. to about 10° C. under acidic conditions. Sanitization according to the invention can comprise inactivation of infectious agents that may contaminate the chromatographic media. The infectious agents can be contaminants of blood products starting material, e.g., plasma. The potential contaminants addressed by the invention include viruses, cellular pathogens, or protein pathogens. Examples include: viral (parvovirus B19, human immunodeficiency virus (HIV), hepatitis viruses, human herpes viruses, cytomegalovirus, Epstein-Barr virus, West Nile virus), bacterial (*Treponema pallidum*, *Neisseria* gonorrhoea, Chlamydia trachomatis, Streptococcus pyogenes, Mycobacterium tuberculosis, Brucella melitensis, Brucella melitensis, Ehrlichia, Staphylococci, Pseudomonas aeruginos) or parasitic (Plasmodium, Trypanosoma cruzi, Babesia microti). The infectious agent can be a pathogenic prion protein (which may be referred to herein as $PrP^{Sc}$; the noninfectious prion species being denoted $PrP^c$; and non-specifically as PrP). Regarding protein therapeutics produced by recombinant or transgenic means, examples of infectious agents include murine retroviruses, bovine spongiform encephalopathy, and scrapie.

In yet another aspect, the invention relates to a method for accomplishing viral inactivation of chromatographic media, sufficient to allow the media to be subsequently utilized in the purification or preparation of materials for therapeutic administration, by contacting the media with a solution of guanidine hydrochloride at a concentration of guanidine hydrochloride from about 3 molar to about 8 molar, and at a temperature from about 0° C. to about 25° C., and at a pH of about 1 to about 5. The solution of guanidine hydrochloride can be at a concentration of guanidine hydrochloride of from about 6 molar to about 8 molar. The solution of guanidine hydrochloride can also be at a concentration of guanidine hydrochloride of about 7 molar. The temperature can be from about 0° C. to about 10° C. The temperature can also be from about 2° C. to about 8° C. The temperature can also be about 4° C. The pH can be from about 2.5 to about 4.5. The pH can also be about 4.

According to the methods of the invention, guanidine hydrochloride concentration, pH, and temperature may be varied within ranges that provide acceptable sanitization of chromatographic media. As noted, at lower temperatures, the solubility of guanidine is enhanced by lowering the pH. However, for particular sanitization applications, low temperature may not be a substantial concern, and sufficiently high guanidine concentrations may be achieved at higher pH. The optimal combination of guanidine hydrochloride concentration, pH, and temperature can be determined by one of skill in the art for specific circumstances based on the guidance provided herein.

In yet another aspect, the invention relates to a method for accomplishing viral inactivation of chromatographic resins having alkaline-labile matrices, resins having alkaline-labile ligands, and/or resins having alkaline-labile ligand linkages by contacting the resins with a solution of guanidine hydrochloride according to the methods of the invention. The resin can have an alkaline-labile matrix or linkage.

The resin can also have an alkaline-labile ligand or ligands, for example benzamidine-SEPHAROSE, heparin-SEPHAROSE, Cibacron Blue-SEPHAROSE and Protein A-SEPHAROSE (cross-linked agarose gel). Pathogen inactivation may be realized within the time course necessary to equilibrate the column resin with the sanitization solution and may be extended as a static or dynamic hold until the desired level of inactivation is achieved.

In one embodiment, the resin comprises a polymeric support with a chemically coupled ligand, which could be a small organic compound or macromolecule such as a protein, carbohydrate or nucleic acid that is susceptible to base hydrolysis or structural damage under alkaline conditions. In another embodiment, the resin is a polymeric support chemically linked to a ligand, which could be a small organic compound or macromolecule such as a protein, carbohydrate or nucleic acid, through a chemical bond that is susceptible to base hydrolysis under alkaline conditions.

In yet another embodiment, the resin is chemically crosslinked, beaded agarose (SEPHAROSE-type) or other polymeric bead support coupled to a ligand which can be a small organic compound or macromolecule such as a protein, carbohydrate or nucleic acid.

The term "inactivation" is here defined as the altering of a unit of pathogen so as to render the unit of pathogen incapable of replication. This is distinct from "total inactivation," where all pathogen units present in a given sample are rendered incapable of replication, or "substantial inactivation," where most of the pathogen units present are rendered incapable of replication.

To appreciate that an "inactivation" method may or may not achieve "total inactivation," it is useful to consider a specific example. A bacterial culture is said to be inactivated if an aliquot of the culture, when transferred to a fresh culture plate and permitted to grow, is undetectable after a certain time period. A minimal number of viable bacteria must be applied to the plate for a signal to be detectable. With the optimum detection method, this minimal number is 1 bacterial cell. With a suboptimal detection method, the minimal number of bacterial cells applied so that a signal is observed may be much greater than 1. The detection method determines a "threshold" below which the "inactivation method" appears to be completely effective (and above which "inactivation" is, in fact, only partially effective).

The same considerations of detection method and threshold exist when determining the sensitivity limit of an inactivation method. Again, "inactivation" means that a unit of pathogen is rendered incapable of replication (or incapable of transmission of disease, e.g. as with pathogenic prion protein).

In the case of inactivation methods for material to be used by humans, whether in vivo or in vitro, the detection method can theoretically be taken to be the measurement of the level of infection with a disease as a result of exposure to the material. The threshold below which the inactivation method is complete is then taken to be the level of inactivation which is sufficient to prevent disease from occurring due to contact with the material. It is recognized that, in this practical scenario, it is not essential that the methods of the present invention result in "total inactivation". That is to say, "substantial inactivation" will be adequate as long as the viable portion is insufficient to cause disease. Thus "substantially all" of a pathogen is inactivated when any viable portion of the pathogen which remaining is insufficient to cause disease. The inactivation method of the present invention can render pathogens substantially inactivated.

Viral Inactivation

The terms "guanidine hydrochloride" and "guanidine.HCl" may be used interchangeably herein. It is known that guanidine hydrochloride can inactivate virus in protein solutions. Virus inactivation can be facilitated by adding guanidine hydrochloride (at concentrations up to ~3M) directly to protein solutions of interest in conjunction with a heating step. Guanidine hydrochloride itself has the ability to inhibit the replication of a small number of viruses, usually at millimolar concentrations. The use of guanidine hydrochloride is known for removal of tightly bound proteins from chromatography resins.

As one aspect of the present invention, it has been demonstrated that solutions of acidified guanidine hydrochloride can be used at approximately 4° C. to inactivate viruses that may remain associated with chromatography resins following the use of such resins to purify proteins from human plasma, plasma fractions, or from other animal or recombinant sources.

Currently, one method of inactivating virus associated with chromatographic resin is to treat the resin with NaOH. While effective, this method is not tolerated by a number of chromatographic resins (including but not limited to benzamidine-SEPHAROSE) that have alkaline-labile matrices or ligands.

Additionally, many chromatographic processes are carried out at a target temperature of 4° C. in order to maintain low levels of bioburden and/or maintain the biological activity of a protein. However, the solubility of guanidine hydrochloride decreases as a function of temperature. According to the present invention, it was discovered that the solubility of high concentrations of guanidine hydrochloride (up to 8 M) at low temperatures (4° C.) could be maintained by acidifying the solution. Additionally, the inventors have demonstrated inactivation of virus in solution at 4° C. using 6.5 M guanidine hydrochloride at pH 4.0. Further, it was demonstrated that this concentration could be lowered to 4 M at pH 3.0 while maintaining effective viral inactivation.

Further, the inventors have demonstrated that chromatographic column-associated virus (benzamidine-SEPHAROSE resin) can be inactivated through the use of high concentrations of guanidine hydrochloride (7.2 M) at pH 3.0. See the Examples below.

Prion Contamination

Although no transmissible spongiform encephalopathy (TSE) infectious agents (pathogenic prion proteins) have been identified in human blood or blood products, recent animal model evidence indicates that the theoretical risk persists. Therefore, it is desirable that any sanitization regimen used to treat production surfaces exposed to plasma or other blood product intermediates during the isolation of biological therapeutics, including chromatography media, remove or inactivate $PrP^{Sc}$, the infectious proteinaceous agent responsible for TSE infectivity.

One defining characteristic of $PrP^{Sc}$ is its resistance to proteinase K digestion. While proteinase K digestion of the normal cellular form of PrP ($PrP^C$) results in total loss of PrP (as assessed by sensitive Western blotting techniques; see Lee, D. et al., J Virol Methods, 84(1):77–89(2000), incorporated herein by reference), digestion of $PrP^{Sc}$ by proteinase K yields a truncated form of the protein identified as $PrP^{RES}$. Loss of proteinase K resistance, as evidenced by loss of $PrP^{RES}$ immunoreactivity, correlates with $PrP^{Sc}$ inactivation.

Chemicals that either hydrolyze or denature $PrP^{Sc}$ are potential clean-in-place reagents. The chaotropic agent guanidine hydrochloride is known to inactivate $PrP^{Sc}$ in solution at near neutral pH (Caughey, et al. J. of Virology. 71:4107–4110 (1997); Manuelidis, L., J. of Neurovirol. 3:62–65(1997)). In support of using acidic guanidine hydrochloride as a clean-in-place agent for chromatography media, the capacity of this formulation to inactivate $PrP^{Sc}$ was investigated. $PrP^{Sc}$ was resuspended in a 4 M guanidine hydrochloride, pH 3 solution and incubated for 1 hour at room temperature. A $\geq 2.5$ log decrease in $PrP^{RES}$ immunoreactivity, as compared to the non-treated control, was observed even with this lower concentration of acidic guanidine. Additionally, treatment of surface adsorbed $PrP^{Sc}$ with 7.2 M guanidine hydrochloride, pH 3 yielded at least a 2.75 log reduction in immunoreactive $PrP^{RES}$ (also 1 hour incubation). The loss of $PrP^{RES}$ immunoreactivity demonstrates that acidic guanidine hydrochloride effectively inactivates $PrP^{Sc}$.

EXAMPLES

Example 1

Viral Inactivation Assay: Column Chromatography

To evaluate viral clearance as one aspect of sanitization of chromatographic media, the following assay was used. The terms "Load," "Elution Peak," etc. as used below in Table 1, correspond to terms as ordinarily used in the art of protein purification.

Column Load material (a dilute protein solution containing the serine protease plasmin at a concentration of approximately 0.9 mg/mL) was "spiked" with the virus of interest (porcine parvovirus; PPV), to a final volume contribution of 10% (i.e., 1 volume of virus solution: 9 volumes of Load). The PPV solution was prepared by propagating the virus in Mini Pig Kidney (MPK) cells, obtained from ATCC (American Type Culture Collection), using Dulbecco's Modified Eagles Medium (Gibco/Life Technologies, Grand Island, N.Y.), containing 10% FBS and NHG (DMEM+10% FBS+NHG). NHG consisted of 0.1 mM nonessential amino acids (Gibco/Life Technologies, Grand Island, N.Y.), 10 mM HEPES (N-[2-Hydroxyethyl]piperazine-N'-[2-ethanesulfonic acid]; Sigma Chemical Company, St Louis, Mo.), gentamicin (0.05 mg/mL; Gibco/Life Technologies, Grand Island, N.Y.) and fungizone (2.5 µg Amphotericin B/mL; Gibco/Life Technologies, Grand Island, N.Y.). PPV was prepared by infecting sub-confluent monolayers of MPK cells at a low multiplicity of infection (moi ranged from 0.1 to 0.01), adding PPV propagation medium (DMEM+10% FBS+NHG) and then incubating the cells at 36° C.–38° C. in a $CO_2$ incubator until advanced CPE was observed. The infected cells were disrupted by freeze thawing and the cell lysates were stored at −70° C. until used. The virus spike was prepared by thawing the virus-infected cell lysates, centrifuging at low speed (e.g. 5000 RPM or 4100× g, 15 minutes, 5° C., SORVALL SLA 600TC rotor) to remove the cell debris and collecting the clarified supernatants for use as the virus spike. The "spiked" Load material was then assayed (see below) to determine the measurable amount of virus (titer) in the Load. This "spiked" Load was then applied to a benzamidine SEPHAROSE column and the chromatography cycle was carried out as normally performed to purify the protein of interest (plasmin). Fractions were collected and their volumes measured during the chromatography cycle. Each fraction was then assayed to determine the amount of virus that partitioned with the particular fraction. The total amount of virus was then calculated for the various fractions by multiplying the titer (usually expressed logarithmically as the number of virus particles per ml) by the volume of the fraction.

The amount of virus clearance is usually reported as the ratio of total virus in the Load to total virus in a particular fraction:

$Log_{10}$[Load Volume×Load Titer/Fraction Volume×Fraction Titer] This is referred to as the Log Reduction Value or "LRV."

Typically the "Elution Peak" material is the fraction of most interest since this usually contains the desired purified protein.

To assay for virus (PPV), half $log_{10}$ (1:3.2) serial dilutions of the samples (spiked-Load, various fractions, etc.) were prepared in Hanks Buffered Saline Solution. Aliquots of these serial dilutions were then added to approximately 60% confluent MPK cells seeded in 96-well tissue culture plates. Just prior to use, the growth medium was removed from the cells and 100 µL of DMEM+2% FBS+NHG was added back to each well. Eight replicates (100 μL aliquots) of each dilution were added to a given row of cells on the plate. In this way, a single plate accommodated up to 12 different dilutions. A single row (8 wells) received only HBSS as a virus-negative control. Cells were then incubated with the various dilutions for 75 minutes at 36° C.–38° C. in a $CO^2$ incubator. After the incubation period, all of the solutions were removed from each well and replaced with the growth media. The plates were then incubated for 7 days at 36° C.–38° C. in a $CO^2$ incubator. After the 7 day incubation period (as in Table 1), the cells were examined microscopically for evidence of virus infection (infection is usually marked by cell death). By assessing the number of infected wells on a plate and taking into consideration the increasing dilutions, a virus titer was calculated. A statistical approach referred to as the method of Spearman and Karber is routinely used to generate the titer values (Spearman, C. and G. Karber, In: Bibrack, B. and G. Wittmann, eds., *Virologische Arbeitsmethoden*. Stuttgart: Fischer Verlag, pp. 37–39 (1974). If a sample was "titrated" and no signs of infection (positives) were observed in those cells that received the undiluted material, the limit of the assay detection was reported as $\leq 0.7$ $\log_{10}$ TCID50/ml (Tissue Culture Infectious Dose, 50% endpoint). This indicated that there were less than 5 virus particles per ml of the sample.

If the sample assayed was toxic to the cells used to detect the virus, this "cytotoxicity" resulted in an increased "limit of detection." Under these circumstances, the first of the serially diluted samples that was not toxic to the cells will dictate the limit of detection. This increased limit of detection was observed when virus was titrated in acidic guanidine hydrochloride. Depending on the cell type, acidic guanidine hydrochloride diluted up to 3.2–3 may still be toxic to the cells, and the reported detection limit would be $\leq 2.8$ $\log_{10}$ TCID50/ml.

Table 1, below, presents a summary of three virus clearance chromatography experiments. The Table illustrates an evaluation of the benzamidine-SEPHAROSE chromatography step used to purify plasmin. These runs were carried out using a non-enveloped virus (porcine parvovirus; PPV) that is known to be very resistant to inactivation by physical and chemical means. The chromatography cycle consists of the following 5 steps: Load, Wash, Elute, Regeneration/Sanitization and Storage. The Regeneration/Sanitization step utilized acidic guanidine hydrochloride (7.2 M guanidine.HCl, 0.1 M acetic acid, pH 3.0). The data in Table 1 show that most of the virus passed through the column and was associated with the Flow Through/Wash fraction. While the amount of virus in the Elution Peak fraction was ~2 $\log_{10}$ lower than that in the Load material, measurable amounts of virus could still be observed coming off of the column. For this reason, the column must be sanitized to inactivate and remove any virus that remains on the column before it can be used again. These circumstances simulated actual cleaning of a column after blood product purification chromatography.

The increase in virus titer in the material collected during the Regeneration/ Sanitization step (relative to the Elution Peak titer) demonstrated that virus was being removed from the column. The subsequent Storage step demonstrated that no measurable virus was present in the effluent following the Regeneration/Sanitization step. The Storage buffer (20% ethanol) is slightly toxic to the cells, hence the limit of detection of $\leq 1.8$ TCID50/mL. The samples marked Pre-Equilibration Fractions were collected from the column effluent as the column was equilibrated with wash buffer on the day after the virus clearance run. The absence of measurable virus in these fractions further demonstrated that the column was effectively sanitized.

TABLE 1

Porcine Parvovirus Clearance Across the Benzamidine-SEPHAROSE Column in a Plasmin Purification Process.

| Experiment Number Virus: PPV Sample | PM-BZ-SV-01 | | | PM-BZ-SV-02 | | | PM-BZ-SV-03 | | | Average |
|---|---|---|---|---|---|---|---|---|---|---|
| | Virus Titer/m $\log_{10}TCID_{50}$ | Total Virus | LRV | Virus Titer/m $\log_{10}TCID_{50}$ | Total Virus | LRV | Virus Titer/m $\log_{10}TCID_{50}$ | Total Virus | LRV | LRV +/− Standard Deviation |
| HBSS Virus Control Start | 5.7 | NA | NA | 5.7 | NA | NA | 5.7 | NA | NA | |
| Virus Spiked Benzamidine Load Start | 5.5 | 7.37 | 0.0 | 5.7 | 7.52 | 0.0 | 5.8 | 7.65 | 0.0 | |
| Flow Through/Wash | 5.2 | 7.11 | 0.3 | 5.0 | 6.82 | 0.7 | 5.0 | 6.84 | 0.8 | |
| Pre-Elution | 4.0 | 5.58 | 1.8 | 3.6 | 5.10 | 2.4 | 3.8 | 5.18 | 2.5 | |
| Elution Peak | 3.8 | 5.69 | 1.7 | 3.5 | 5.33 | 2.2 | 3.8 | 5.70 | 2.0 | 1.9 +/− 0.3 |
| Regeneration/Sanitization | 5.2 | 7.21 | 0.2 | 3.7 | 5.79 | 1.7 | 4.6 | 6.66 | 1.0 | |
| Storage | $\leq 1.8$ | $\leq 3.54$ | $\geq 3.8$ | $\leq 1.8$ | $\leq 3.55$ | $\geq 4.0$ | $\leq 1.8$ | $\leq 3.54$ | $\geq 4.1$ | |
| HBSS Virus Control End - Day 1 | 5.5 | NA | NA | 5.5 | NA | NA | 5.8 | NA | NA | |
| Pre-Equilibrium Fraction 1 - Day 2 | $\leq 0.7$ | NA | NA | $\leq 0.7$ | NA | NA | $\leq 0.7$ | NA | NA | |
| Pre-Equilibrium Fraction 2 - Day 2 | $\leq 0.7$ | NA | NA | $\leq 0.7$ | NA | NA | $\leq 0.7$ | NA | NA | |
| Pre-Equilibrium Fraction 3 - Day 2 | $\leq 0.7$ | NA | NA | $\leq 0.7$ | NA | NA | $\leq 0.7$ | NA | NA | |
| HBSS Virus Control End - Day 2 | 4.7 | NA | NA | 4.7 | NA | NA | 5.1 | NA | NA | |
| $\log_{10}$ Virus Recovered | | 7.48 | | | 6.88 | | | 7.08 | | |

*PPV = Porcine Parvovirus
*HBSS = Hank's Balanced Salt Solution
*LRV = Log Reduction Value Example 2

Sanitization of Benzamidine-SEPHAROSE

Benzamidine-SEPHAROSE resin presents a sanitization challenge in that the resin is not stable to high ($\geq 9$) and low ($\leq 1$) pH conditions. As such, the pH stability characteristics preclude the use of NaOH for sanitization as is routinely done for other more stable resins.

A series of solutions were evaluated for the capacity to inactivate porcine parvovirus (PPV), a durable (to physicochemical inactivation techniques) model virus. The requirements for the solution were:

1) virus (PPV) kill to the detection limit of the assay (see Example 1), 2) effective at 4° C., and 3) compatibility with the benzamidine-SEPHAROSE resin.

Solutions tested included a variety of alcohols, detergents, and chaotropic agents including guanidine hydrochloride (Table 2). An initial screen identified 8 M guanidine hydrochloride as effective at killing virus to the detection limit of the assay at room temperature. Inactivation at 4° C. could not be evaluated initially with 8 M guanidine as precipitation occurred at the lower temperature. Lower concentrations (6 M) of guanidine hydrochloride with 25% alcohol provided a solution stable (no precipitation) at 4° C., however, it was only partially effective at killing virus. A series of experiments were performed to identify conditions under which 8 M guanidine hydrochloride would stay in solution. By acidifying (to pH 4.0 or 3.0) the 8 M guanidine, a solution was obtained that did not precipitate at 4° C. Additionally, when mixed with virus (1 part virus:9 parts acidic guanidine hydrochloride; final guanidine hydrochloride concentration=7.2 M) inactivation to the limit of detection occurred within 30 minutes at 4° C. Similar experiments were carried out treating the benzamidine-SEPHAROSE column with 7.2 M guanidine hydrochloride, pH 3.0, following a viral clearance evaluation run. This treatment demonstrated effective virus (PPV and bovine viral diarrhea virus (BVDV)) inactivation to the limit of assay detection as described above.

TABLE 2

Various Solutions Tested for the Ability to Inactivate PPV.

| Sample Results for 3 hour samples | Virus Titer $\text{Log}_{10}$ $\text{TCID}_{50}/\text{ml}$ | Virus Reduction $\text{Log}_{10} \text{TCID}_{50}/\text{ml}$ | Comments |
|---|---|---|---|
| Positive Control - 3 hours | 6.1 | NA | |
| Sample 1 25% SDA | 6.0 | 0.1 | |
| Sample 2 50% SDA | 5.7 | 0.4 | |
| Sample 3 75% SDA | 5.7 | 0.4 | |
| Sample 4 100% SDA | 5.6 | 0.5 | |
| Sample 5 8M GH (RT) | ≤2.8 | ≥3.3 | No positives Toxic @ -2 |
| Sample 6 6M GH/25% SDA | [1]4.2 (3.5) | 1.9 (2.6) | |
| Sample 7 3M GH/25% SDA | [1]5.7 (5.7) | 0.4 (0.4) | |
| Sample 8 3M GH/25% SDA/100mMAA | [1]6.0 (5.5) | 0.1 (0.6) | |
| Sample 9 100mM AA/ 25% SDA | [1]6.1 (5.1) | 0.0 (1.0) | |
| Sample 10 0.2% BA/ 0.5% Hib./100mM AA | 5.8 | 0.3 | |
| Sample 11 20mMPA/ 100mMAA | ≤3.3 | ≥2.8 | No positives Toxic to -4 |
| Sample 12 2% SDS/ 100mMAA (RT) | ≤3.3 | ≥2.8 | No positives Toxic to -4 |
| Sample 13 6.75 Urea/ 25% SDA (RT) | 3.7 | 2.4 | |

[1]The values in parentheses are duplicate data from two different operators. Virus reduction was calculated by subtracting the titer of the experimental sample from the titer of the positive control. Note that those treatments resulting in complete viral inactivation are shown with a gray background.
Abbreviations:
SDA: Solvent Denatured Alcohol; GH: Guanidine.HCl; AA: Acetic Acid; BA: Benzyl Alcohol; Hib.: Hibitane; PA: Peracetic Acid; SDS: Sodium Dodecyl Sulfate

TABLE 3

Inactivation of PPV in 7.2M Guanidine Hydrochloride at 4° C.

| Sample | Virus Titer $\text{Log}_{10} \text{TCID}_{50}/\text{ml}$ | Virus Reduction $\text{Log}_{10} \text{TCID}_{50}/\text{ml}$ | Comments |
|---|---|---|---|
| Positive Control | 5.2 | NA | |
| 7.2M Guanidine + 100mM acetic acid (0 hr) | 3.3 | 1.9 | |
| 7.2M Guanidine + 100mM acetic acid (0.5 hr) | ≤2.3 | ≥2.9 | toxic @ -2 |
| 7.2M Guanidine + 100mM acetic acid (1 hr) | ≤2.3 | ≥2.9 | toxic @ -2 |
| 7.2M Guanidine + 100mM acetic acid (2 hr) | ≤2.3 | ≥2.9 | toxic @ -2 |
| 7.2M Guanidine + 100mM acetic acid (3 hr) | ≤2.3 | ≥2.9 | toxic @ -2 |

Virus reduction was calculated by subtracting the titer of the experimental sample from the titer of the positive control.

Example 3

Inactivation of Prion Pathogens

To further investigate acidic guanidine hydrochloride as a clean-in-place agent for chromatography media, the capacity of this formulation to inactivate $\text{PrP}^{Sc}$ (pathogenic prion protein, the pathogenic agent in transmissible spongiform encephalopathy or TSE) was examined. $\text{PrP}^{Sc}$ was resuspended in a 4M guanidine hydrochloride, pH 3 solution and incubated for 1 hour at room temperature. A ≧2.5 log decrease in $\text{PrP}^{RES}$ immunoreactivity, as compared to the non-treated control, was observed even with this lower concentration of acidic guanidine. Additionally, treatment of surface adsorbed $PrP^{Sc}$ with 7.2 M guanidine hydrochloride, pH 3 yielded a 2.75 log reduction in immunoreactive $PrP^{RES}$. The loss of $PrP^{RES}$ immunoreactivity demonstrates the effectiveness of guanidine hydrochloride, pH 3 to inactivate $PrP^{Sc}$ (see Lee, D. et al., *J Virol Methods,* 84(1):77–89 (2000), incorporated herein by reference).

What is claimed is:

1. A method of sanitizing chromatographic media, the method comprising contacting the media with a solution of guanidine hydrochloride at a pH of about 1 to about 5, for a time and at a temperature sufficient to achieve a desired level of sanitization while preserving desirable characteristics of the media.

2. The method of claim 1, wherein the sanitizing includes viral inactivation.

3. The method of claim 2, wherein the viral inactivation is sufficient to allow the sanitized media to be subsequently utilized in the purification or preparation of materials for therapeutic administration.

4. The method of claim 1, wherein chromatographic media is exposed to the solution of guanidine hydrochloride at a temperature from about 0° C. to about 25° C.

5. The method of claim 1, wherein the temperature is about 4° C.

6. The method of claim 1, wherein the solution of guanidine hydrochloride is at a concentration of guanidine hydrochloride from about 3 molar to about 8 molar.

7. The method of claim 1, wherein the concentration of guanidine hydrochloride is about 7 molar.

8. The method of claim 1, wherein the solution of guanidine hydrochloride is at a pH from about 2.5 to about 4.5.

9. The method of claim 1, wherein the chromatographic media is selected from the group consisting of resins having alkaline-labile matrices and resins having alkaline-labile ligands.

10. A method of sanitizing chromatographic media, the method comprising contacting the media with a solution of guanidine hydrochloride at a concentration of guanidine hydrochloride from about 3 molar to about 8 molar, at a temperature from about 0° C. to about 10° C., and at a pH of from about 1 to about 5.

11. The method of claim 10, wherein the sanitizing comprises contacting the chromatographic media with the solution under conditions sufficient for inactivation of infectious agents that may contaminate the chromatographic media.

12. The method of claim 11, wherein the infectious agents are viral, cellular, or pathogenic protein contaminants of blood products.

13. The method of claim 12, wherein the contaminants of blood products are selected from the group consisting of parvovirus B19, human immunodeficiency virus (HIV), hepatitis viruses, human herpes viruses, cytomegalovirus, Epstein-Barr virus, West Nile virus, *Treponema pallidum, Neisseria gonorrhoea, Chlamydia trachomatis, Streptococcus pyogenes, Mycobacterium tuberculosis, Brucella melitensis, Brucella melitensis, Ehrlichia, Staphylococci, Pseudomonas aeruginos, Plasmodium, Trypanosoma cruzi, Babesia microti*, and pathogenic prion protein.

14. The method of claim 12, wherein the infectious agent is a virus selected from the group consisting of parvovirus B19, human immunodeficiency virus (HIV), hepatitis viruses, human herpes viruses, cytomegalovirus, Epstein-Barr virus, and West Nile virus.

15. The method of claim 12, wherein the infectious agent is a prion protein.

16. A method for inactivation a virus associated with chromatographic media sufficient to allow the media to be subsequently utilized in the purification or preparation of materials for therapeutic administration, the method comprising contacting the media with a solution of guanidine hydrochloride at a concentration of guanidine hydrochloride from about 3 molar to about 8 molar, at a temperature from about 0° C. to about 10° C., and at a pH of about 1 to about 5.

17. The method of claim 16, wherein the solution of guanidine hydrochloride is at a concentration of guanidine hydrochloride of about 7 molar.

18. The method of claim 16, wherein the temperature is about 4° C.

19. The method of claim 16, wherein the pH is about 4.

20. A method accomplishing viral inactivation of chromatographic resins selected from the group consisting of resins having alkaline-labile matrices and resins having alkaline-labile ligands, the method comprising contacting the resins with a solution of guanidine hydrochloride at a concentration of guanidine hydrochloride from about 3 molar to about 8 molar, at a temperature from about 0° C. to about 10° C., and at a pH from about 2.5 to about 4.5.

21. The method of claim 20, wherein the concentration of guanidine hydrochloride is about 7 molar.

22. The method of claim 20, wherein the temperature is about 4° C.

23. The method of claim 20, wherein the pH is about 4.

24. The method of claim 20, wherein the resin has an alkaline-labile linkage.

25. The method of claim 20, wherein the resin is selected from the group consisting of benzamidine-cross-linked agarose gel, heparin-cross-linked agarose gel, Cibacron Blue-cross-linked agarose gel, and Protein A-cross-linked agarose gel.

26. The method of claim 20, wherein the resin comprises an alkali-labile ligand or ligand linkage.

27. A method of sanitizing chromatographic media, the method comprising contacting the media with a solution of guanidine hydrochloride at a pH of about 1 to about 5, for a time and at a temperature sufficient to achieve a desired level of sanitization while preserving desirable characteristics of the media;

recovering the media; and testing the media to confirm a desired level of sanitization.

28. A method of sanitizing chromatographic media, the method comprising contacting the media with a solution of guanidine hydrochloride at a concentration of guanidine hydrochloride from about 3 molar to about 8 molar, at a temperature from about 0° C. to about 10° C., and at a pH from about 2.5 to about 4.5, recovering the media; and testing the media to confirm a desired level of sanitization.

* * * * *